[54] 3-[PYRIDINYLALKYL AND PIPERIDINYLALKYL]-2,3,4,4a-TETRAHYDRO-1H-PYRAZINO[1,2-a]QUINOXALIN-5(6H)-ONES

[75] Inventor: Meier E. Freed, Paoli, Pa.

[73] Assignee: American Home Products Corporation, New York, N.Y.

[21] Appl. No.: 40,609

[22] Filed: May 21, 1979

[51] Int. Cl.$^2$ .................. A61K 31/495; C07D 487/04
[52] U.S. Cl. .................................... 424/250; 544/346
[58] Field of Search ........................ 544/346; 424/250

[56] References Cited

U.S. PATENT DOCUMENTS

| | | | |
|---|---|---|---|
| 4,032,639 | 6/1977 | Freed et al. | 544/346 |
| 4,089,958 | 5/1978 | Freed et al. | 544/346 |

*Primary Examiner*—Paul M. Coughlan, Jr.
*Attorney, Agent, or Firm*—Arthur G. Seifert

[57] ABSTRACT

Disclosed herein are compounds of the formula:

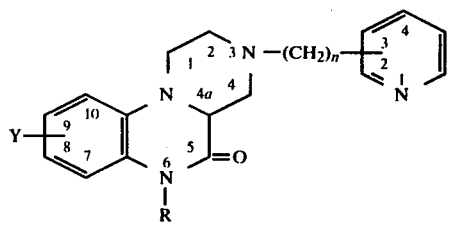

or

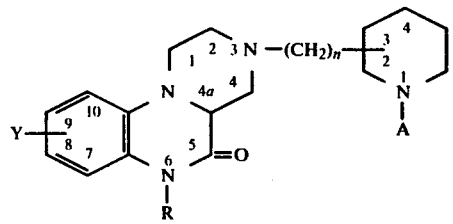

wherein
n is an integer from 1 to 8;
R is hydrogen or lower alkyl;
Y is hydrogen, lower alkyl, lower alkoxy, chlorine, fluorine, or trifluoromethyl in the 7, 8, or 9 position;
A is hydrogen, lower alkyl, phen(lower)alkyl, or diphenyl(lower)alkyl; and
the pyridinyl or piperidinyl moiety is joined to the alkylene bridging group at the 2 or 4 position; or non-toxic acid addition salts thereof. These compounds exhibit hypotensive effects in hypertensive animals and also exhibit anti-secretory properties.

54 Claims, No Drawings

3-[PYRIDINYLALKYL AND PIPERIDINYLALKYL]-2,3,4,4a-TETRAHYDRO-1H-PYRAZINO[1,2-a]QUINOXALIN-5(6H)-ONES

This invention comprises 2,3,4,4a-tetrahydro-1H-pyrazino[1,2-a]quinoxalin-5(6H)-one compounds which have a pyridinylalkyl or a piperidinylalkyl moiety attached to the nitrogen of the pyrazino portion of said tricyclic ring system, i.e. at the three position thereof. The compounds of the invention exhibit anti-hypertensive effects when administered to hypertensive animals and also exhibit anti-secretory properties.

The 2,3,4,4a-tetrahydro-1H-pyrazino[1,2-a]quinoxalin-5(6H)-ones, from which the pyridinylalkyl and piperidinylalkyl compounds of the invention are prepared, are described in U.S. Pat. Nos. 4,032,639, 4,089,958, and 4,138,567, dated June 28, 1977, May 16, 1978, and Feb. 6, 1979, respectively, issued to M. Freed and J. Potoski.

In its generic aspect, the invention comprises chemical compounds of the formula:

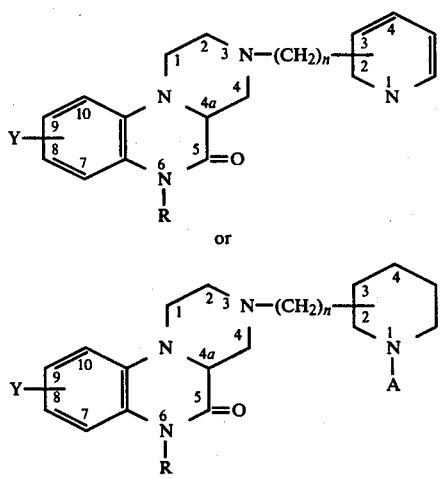

wherein
n is an integer from 1 to 8;
R is hydrogen or lower alkyl;
Y is hydrogen, lower alkyl, lower alkoxy, chlorine, fluorine, or trifluoromethyl, in the 7, 8, or 9 position;
A is hydrogen, lower alkyl, phen(lower)alkyl, or diphenyl(lower)alkyl; and
the pyridinyl or piperidinyl moiety is joined to the alkylene bridging group at the 2 or 4 position; or
a non-toxic acid addition salt thereof.

The compounds of Formula Ia or Ib exert an antihypertensive effect in warm-blooded animals and also inhibit gastric secretion in warm-blooded animals, as evidenced by pharmacological evaluation in standard test procedures.

In its subgeneric aspects this invention comprises the following preferred embodiments:

The compounds of Formula Ia, herein called the "pyridinylalkyl compounds" of the invention, in which n is 1 to 5;

The pyridinylalkyl compounds in which Y is hydrogen, fluorine, or trifluoromethyl; and the pyridinylalkyl compounds in which Y is in the 8 position; particularly, such compounds in which Y is hydrogen, 8-fluoro, or 8-trifluoromethyl;

Those pyridinylalkyl compounds in which R is hydrogen or methyl;

Those pyridinylalkyl compounds in which Y and R are each hydrogen;

The compounds of Formula Ib, herein called the "piperidinylalkyl compounds" of the invention, in which n is 1 to 5; particularly, those compounds in which n=2;

The piperidinylalkyl compounds in which Y is hydrogen, fluorine, or trifluoromethyl; and the piperidinylalkyl compounds in which Y is in the 8 position; particularly, such compounds in which Y hydrogen, 8-fluoro, or 8-trifluoromethyl;

Those piperidinylalkyl compounds in which R is hydrogen or methyl; and those piperidinylalkyl compounds in which A is hydrogen or diphenylmethyl.

A further aspect of the invention provides a method for relieving hypertension in warm-blooded animals which comprises administering to an animal in need thereof an anti-hypertensive effective amount of a compound of Formula Ia or Ib. Preferred embodiments for use in treating hypertension are as follows:

The compounds of Formula Ia (the pyridinylalkyl compounds) in which n is 1 to 5;

The pyridinylalkyl compounds in which Y is hydrogen, fluorine, or trifluoromethyl; and the pyridinylalkyl compounds in which Y is in the 8 position; particularly such compounds in which Y is hydrogen, 8-fluoro, or 8-trifluoromethyl;

Those pyridinylalkyl compounds in which R is hydrogen or methyl;

Those pyridinylalkyl compounds in which Y and R are each hydrogen;

The compounds of Formula Ib (the piperidinylalkyl compounds) in which n is 1 to 4;

The piperidinylalkyl compounds in which Y is hydrogen or trifluoromethyl; and the piperidinylalkyl compounds in which Y is in the 8 position; particularly, such compounds in which Y is hydrogen or 8-fluoro;

The piperidinylalkyl compounds in which R is hydrogen; and the piperidinylalkyl compounds in which A is hydrogen or diphenylmethyl.

The following compounds are especially preferred as anti-hypertensive agents:
2,3,4,4a-tetrahydro-3-[2-(2-pyridinyl)ethyl]-1H-pyrazino[1,2-a]quinoxalin-5(6H)-one;
8-fluoro-2,3,4,4a-tetrahydro-3-[2-(4-pyridinyl)ethyl]-1H-pyrazino[1,2-a]quinoxalin-5(6H)-one;
2,3,4,4a-tetrahydro-8-trifluoromethyl-3-[2-(2-pyridinyl)ethyl]-1H-pyrazino[1,2-a]quinoxalin-5(6H)-one;
2,3,4,4a-tetrahydro-3-[(4-pyridinyl)methyl]-1H-pyrazino-[1,2-a]quinoxalin-5(6H)-one;
2,3,4,4a-tetrahydro-3-[3-(4-pyridinyl)propyl]-1H-pyrazino[1,2-a]quinoxalin-5(6H)-one;
8-fluoro-2,3,4,4a-tetrahydro-3-[(4-pyridinyl)methyl]-1H-pyrazino[1,2-a]quinoxalin-5(6H)-one;
2,3,4,4a-tetrahydro-3-[4-(4-pyridinyl)butyl]-1H-pyrazino[1,2-a]quinoxalin-5(6H)-one;
8-fluoro-2,3,4,4a-tetrahydro-3-[4-(4-pyridinyl)butyl]-1H-pyrazino[1,2-a]quinoxalin-5(6H)-one;
2,3,4,4a-tetrahydro-6-methyl-3-[(4-pyridinyl)methyl]-1H-pyrazino[1,2-a]quinoxalin-5(6H)-one;
2,3,4,4a-tetrahydro-3-[5-(2-pyridinyl)pentyl]-1H-pyrazino[1,2-a]quinoxalin-5(6H)-one;
2,3,4,4a-tetrahydro-3-[5-(4-pyridinyl)pentyl]-1H-pyrazino[1,2-a]quinoxalin-5(6H)-one;

2,3,4,4a-tetrahydro-3-[2-(4-piperidinyl)ethyl]-1H-pyrazino[1,2-a]quinoxalin-5(6H)-one;

2,3,4,4a-tetrahydro-3-[2-(4-[1-diphenylmethyl]-piperidinyl)ethyl]-1H-pyrazino[1,2-a]quinoxalin-5(6H)-one;

2,3,4,4a-tetrahydro-8-trifluoromethyl-3-[2-(2-piperidinyl)ethyl]-1H-pyrazino[1,2-a]quinoxalin-5(6H)-one.

As used herein and in the claims, the term "(lower)alkyl" means an aliphatic hydrocarbon group containing up to three carbon atoms, i.e. the methyl, ethyl propyl, or isopropyl groups. The methyl group is especially preferred. The term "(lower)alkoxy" means an aliphatic ether group having up to three carbon atoms, i.e. methoxy, ethoxy, propoxy, or isopropoxy. The methoxy group is especially preferred. The term "phen(lower)alkyl" means a group in which the phenyl group is attached to an aliphatic hydrocarbon chain containing up to three carbon atoms, e.g. the benzyl, phenethyl, or phenpropyl groups. The term "diphenyl(lower)alkyl" means an aromatic hydrocarbon group in which two phenyl groups are attached to an aliphatic hydrocarbon chain containing up to three carbon atoms, e.g. 1-(diphenylmethyl), 1-(1,2-diphenylethyl), or 2-(1,3-diphenylpropyl). Such diphenyl(lower)alkyl group is also bonded to the piperidinyl nitrogen via the aliphatic hydrocarbon chain.

Preparation

The general method of synthesis of the compounds of the invention is shown below:

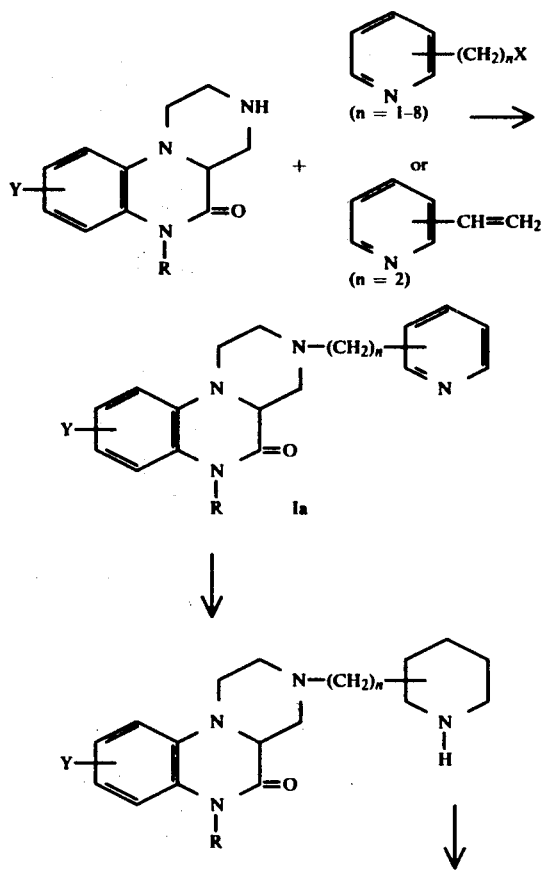

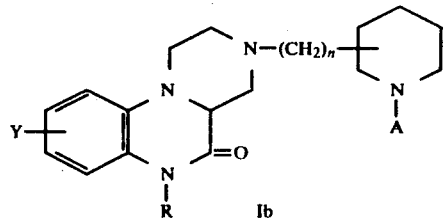

As shown above, the pyridinylalkyl compounds of the invention are prepared by reacting the appropriately substituted 2,3,4,4a-tetrahydro-1H-pyrazino[1,2-a]quinoxalin-5(6H)-one with the desired pyridinyl alkyl halide, preferably the chloride. This reaction is carried out in the presence of an acid scavenger such as trimethylamine, diisopropylethylamine or a metal carbonate, with trimethylamine being preferred. Suitable solvents are acetone, methylethylketone, acetonitrile, ethanol, or 2-propanol. The reaction is normally carried out at the reflux temperature of the solvent.

Where n=2, the preferred synthesis is a Michael Addition of 2- or 4-vinylpyridine to the desired 2,3,4,4a-tetrahydro-1H-pyrazino[1,2-a]quinoxalin-5(6H)-one. This reaction is carried out using a lower alcohol, preferably methanol, as a solvent, in the presence of acetic acid. This reaction is also run at the reflux temperature of the solvent.

In order to make a desired piperidinylalkyl compound of the invention, the appropriately substituted pyridinylalkyl compound of the invention is prepared and then reduced to the piperidinyl form. Hydrogen in the presence of a catalyst is the preferred reducing agent. The preferred catalyst system is a platinum dioxide catalyst in an aqueous hydrochloric acid-ethanol solution. Palladium (in an acetic acid solution, 70°-80° C. temperatures required), rhodium/aluminum or rhodium/carbon catalysts may also be used. In addition to the acetic acid and aqueous hydrochloric acid—alcohol catalytic reaction solutions just mentioned, ethanol, methanol, and dimethylformamide solvent systems may be used for this hydrogenation reaction. In order to avoid hydrogenation of the benzene portion of the tricyclic ring, moderate pressures (under 60 p.s.i.) and temperatures (25°-40° C.) should generally be used. The selection of the appropriate solvent/catalyst combination and reaction conditions will be apparent to those skilled in the art.

As shown in the reaction diagram above, the piperidinylalkyl compounds of the invention in which A is other than hydrogen are prepared from the appropriately substituted piperidinylalkyl compound in which A=H. This is accomplished by the alkylation of the latter with the desired (lower)alkyl halide, phen(lower)alkyl halide, or diphen(lower)alkyl halide. This reaction is carried out in the presence of an acid scavenger such as trimethylamine, diisopropylethylamine, a metal carbonate or a combination of a metal carbonate and trimethylamine. Suitable solvents are acetone, methylethylketone, acetonitrile, ethanol or 2-propanol. The reaction is conveniently carried out at the reflux temperature of the solvent.

The compounds of Formula Ia or Ib as obtained in the processes depicted above, and the appropriate intermediates thereto, may be isolated and purified in a conventional manner. It is furthermore appreciated that in the various processes hereinbefore described, factors such as solvent, pressure, and temperatures are not critical (except to the extent indicated in the reduction process) and the selection of a solvent, pressure, or temperature will be apparent to one skilled in the art of organic chemistry.

The 2,3,4,4a-tetrahydro-1H-pyrazino[1,2-a]quinoxalin-5(6H)-ones used as starting materials in the production of the pyridinylalkyl and piperidinylalkyl compounds of the invention may be prepared by the methods described in U.S. Pat. Nos. 4,032,639, 4,089,958, and 4,138,567 (all previously cited). The description of the preparation of said starting compounds contained in said patents, including the examples contained therein, is incorporated herein and made a part hereof.

Since the compounds of Formula Ia or Ib possess an asymmetric carbon atom optical enantiomorphs are possible, and the compounds of the invention may be in the form of the pure enantiomorph or mixtures thereof, such as the racemates.

The compounds of Formula Ia or Ib may be obtained in the form of the pure enantiomorph either by resolving a desired racemic product or by resolving a racemic starting material or intermediate at any convenient stage of the synthesis. Methods of carrying out the resolution are well-known in the art of chemistry. For example, the desired racemate may be treated with an optically active carboxylic acid and the optically active addition salts may be separated by standard techniques.

The compounds of Formula Ia or Ib may exist either in the form of the free base or the acid addition salt. Methods for converting one such form to another will be obvious to one skilled in the art of chemistry.

For pharmacological use, the compounds of Formula Ia or Ib may be administered in the form of an acid addition salt of a non-toxic organic or inorganic acid. The salts may be prepared by methods well-known in the art. Appropriate salts are those formed from the following acids: hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic, and benzenesulfonic. Such salts are included in the scope of the invention.

Pharmacological Activity

The compounds of the invention are effective in lowering blood pressures as shown in standard tests using hypertensive rats. Such tests are conducted on spontaneously or surgically hypertensive rats. Test groups and control groups usually consist of 4–6 rats, and the test compounds and reference compounds are administered either orally or intraperitoneally. Systolic blood pressures are measured by an indirect technique using the Decker Caudal Plethysmograph or other appropriate sensor, and readings are taken prior to drug administration and periodically thereafter, for example at 1.5, 4, and 24 hours after administration. Results are analyzed statistically. Reference compounds used include clonidine, hydralazine, guanethidine, methyldopa, and reserpine.

When administered in doses of 1–75 mg/kg., verious compounds of the invention demonstrate slight of marked abilities to reduce blood pressures. The antihypertensive activity of a compound is rated as follows:

| Activity | Systolic Decrease in Blood Pressure |
|---|---|
| Not Significant (NS) | <15 mm. Hg. |
| Borderline (BDL) | 15–25 |
| Slight (SLT) | 25–35 |
| Moderate (MOD) | 25–50 |
| Marked (MKD) | over 50 |

When tested in spontaneously hypertensive rats as described above, compounds of Formula Ia or Ib gave the following results:

| Compound | Dose (mg/kg.) | Activity (See Above) |
|---|---|---|
| 2,3,4,4a-tetrahydro-3-[2-(4-pyridinyl)-ethyl]-1H-pyrazino[1,2-a]quinoxalin-5(6H)-one | 25 | * |
| | 5 | NS |
| 2,3,4,4a-tetrahydro-3-[2-(2-pyridinyl)-ethyl]-1H-pyrazino-[1,2-a]quinoxalin-5(6H)-one | 75 | MKD |
| | 25 | MKD |
| | 10 | MKD |
| | 5 | SLT |
| | 2.5 | SLT |
| 8-fluoro-2,3,4,4a-tetrahydro-3-[2-(4-pyridinyl)ethyl]-1H-pyrazino[1,2-a]-quinoxalin-5(6H)-one | 75 | MKD |
| | 25 | MKD |
| | 10 | MOD |
| | 5 | SLT |
| | 2.5 | BDL |
| 8,9-dichloro-2,3,4,4a-tetrahydro-3-[2-(4-pyridinyl)ethyl]-1H-pyrazino[1,2-a]-quinoxalin-5(6H)-one | 75 | MKD |
| | 50 | SLT |
| | 25 | BDL |
| 2,3,4,4a-tetrahydro-3-[2-(4-pyridinyl)-ethyl]-8-trifluoromethyl-1H-pyrazino-[1,2-a]quinoxalin-5(6H)-one | 75 | MKD |
| | 50 | MOD |
| | 10 | NS |
| 2,3,4,4a-tetrahydro-8-trifluoromethyl-3-[2-(2-pyridinyl)ethyl]-1H-pyrazino-[1,2-a]-quinoxalin-5(6H)-one | 25 | MKD |
| | 10 | MKD |
| | 5 | BDL |
| 2,3,4,4a-tetrahydro-3-[(4-pyridinyl)-methyl]-1H-pyrazino[1,2-a]quinoxalin-5(6H)-one | 75 | MKD |
| | 10 | MKD |
| | 5 | MOD |
| | 2.5 | BDL |
| | 1 | NS |
| 2,3,4,4a-tetrahydro-3-[3-(4-pyridinyl)-propyl]-1H-pyrazino[1,2-a]quinoxalin-5(6)-one | 75 | ** |
| | 25 | MKD*** |
| | 10 | MKD |
| | 5 | MKD |
| | 2.5 | MOD-MKD |
| | 1 | BDL |
| 8-fluoro-2,3,4,4a-tetrahydro-3-[(4-pyridinyl)methyl]-1H-pyrazino[1,2-a]quinoxalin-5(6H)-one | 75 | MKD |
| | 25 | MKD-MOD |
| | 10 | MKD |
| | 5 | SLT |
| | 2.5 | BDL |
| | 1 | NS |
| | 0.5 | NS |
| 2,3,4,4a-tetrahydro-3-[2-(4-piperidinyl)-ethyl]-1H-pyrazino[1,2-a]quinoxalin-5(6H)-one | 75 | MKD |
| | 50 | MKD |
| | 10 | MOD |
| | 5 | NS |
| | 2.5 | NS |
| 2,3,4,4a-tetrahydro-3-[2-(2-piperidinyl)-ethyl]-1H-pyrazino[1,2-a]quinoxalin-5(6H)-one | 75 | BDL |
| 8-fluoro-2,3,4,4a-tetrahydro-3-[2-(4-piperidinyl)ethyl]-1H-pyrazino[1,2-a]-quinoxalin-5(6H)-one | 75 | MKD |
| | 50 | SLT |
| | 25 | BDL |
| 3-[2-[1-(diphenylmethyl)-4-piperidinyl]-ethyl]-1H-pyrazino[1,2-a]quinoxalin-5(6H)-one | 25 | MKD |
| | 10 | MOD |
| | 5 | NS |
| | 2.5 | NS |
| 2,3,4,4a-tetrahydro-8-trifluoromethyl-3-[2-(2-piperidinyl)ethyl]-1H-pyrazino-[1,2-a]quinoxalin-5(6H)-one | 75 | MOD-MKD |
| | 25 | BDL |
| 2,3,4,4a-tetrahydro-3-[2-(4-piperidinyl)-ethyl]-8-trifluoromethyl-1H-pyrazino- | 75 | SLT-MOD |
| | 75 | BDL-SLT |

| Compound | Dose (mg/kg.) | Activity (See Above) |
|---|---|---|
| [1,2-a]quinoxalin-5(6H)-one | | |

*Blood pressure could not be read.
**Toxic 3 of 4 dead at 4 hours.
***1 of 4 dead after 24 hours.

A number of standard pharmacological tests may also be employed to demonstrate the effectiveness of the compounds of the invention in inhibiting gastric secretions. Such anti-secretory activity is also evidence of anti-ulcer activity. One such test is a modification of the method of Shay et al., Gastroenterology, 26, 906–913 (1954). In this procedure male Charles River rats weighing 200–300 grams are deprived of food but not water for 24 hours prior to use. Water is, however, withheld during the experiment. The rats are weighed, anesthetized with ether and the pylorus ligated according to the method of Shay et al. Treatment or vehicle control is then administered interduodenally (i.d.) or subcutaneously (s.c.). Rats are housed 2/cage and sacrificed with $CO_2$ four hours after ligation. The stomachs are removed, rinsed, and contents emptied into a graduated centrifuge tube. The tubes are centrifuged for 20 minutes at 2,000 RPM and the volume of gastric juce recorded. Any samples obviously contaminated by feces, food, or hemolysis are eliminated. An aliquot of each is frozen for later analysis of $Na^+$, $K^+$, and $Cl^-$ concentration. The pH is measured and 1 ml. of gastric juice is titrated with 0.1 NaOH to a pH of 7.0–7.4. The data are analyzed for either a Student's t-test or an analysis of variance depending upon which test is appropriate.

When administered according to this modified Shay et al. procedure in doses of 25 or 32 mg/kg. a number of compounds of this invention exhibit anti-secretory properties. The following compounds inhibited gastric secretion by 50 percent or more at these doses:
2,3,4,4a-tetrahydro-3-[2-(2-pyridinyl)ethyl]-1H-pyrazino-[1,2-a]quinoxalin-5(6H)-one;
8-fluoro-2,3,4,4a-tetrahydro-3-[2-(4-pyridinyl)ethyl]-1H-pyrazino[1,2-a]quinoxalin-5(6H)-one;
2,3,4,4a-tetrahydro-3-[2-(4-pyridinyl)ethyl]-8-trifluoromethyl-1H-pyrazino[1,2-a]quinoxalin-5(6H)-one;
2,3,4,4a-tetrahydro-8-trifluoromethyl-3-[2-(2-pyridinyl)ethyl]-1H-pyrazino[1,2-a]quinoxalin-5(6H)-one;
2,3,4,4a-tetrahydro-3-[(4-pyridinyl)methyl]-1H-pyrazino-[1,2-a]quinoxalin-5(6H)-one;
2,3,4,4a-tetrahydro-3-[3-(4-pyridinyl)propyl]-1H-pyrazino[1,2-a]quinoxalin-5(6H)-one;
2,3,4,4a-tetrahydro-3-[2-(4-piperidinyl)ethyl]-8-trifluoromethyl-1H-pyrazino[1,2-a]quinoxalin-5(6H)-one.

At a dose of 32 mg/kg. 2,3,4,4a-tetrahydro-3-[2-(4-pyridinyl)ethyl]-1H-pyrazino[1,2-a]quinoxalin-5(6H)-one elicited significant anti-secretory activity, but at a lower dose of 2 mg/kg. showed no such activity.

When employed to lower blood pressures or to reduce gastric secretions, the effective dosage of the substance active for such treatment will vary according to the particular compound being employed, the severity and nature of condition being treated, and the particular subject being treated. Therapy should be initiated at lower doses (in mg/kg/day) in the effective ranges given above for the prescribed activity, the dosage thereafter being increased, if necessary, to produce the desired anti-hypertensive or anti-secretory effect.

Further, when employed as anti-ulcer, anti-secretory, or anti-hypertensive agents, the compounds of the invention, or pharmacologically acceptable acid addition salts thereof, may be administered alone or in combination with pharmaceutically acceptable carriers. The proportion and nature of such carriers would be determined by the solubility and other chemical properties of the compound selected, the chosen route of administration, and standard pharmaceutical practice.

The following examples further illustrate the best mode of practicing this invention.

EXAMPLE 1

2,3,4,4a-Tetrahydro-3-[2-(4-Pyridinyl)Ethyl]-1H-Pyrazino[1,2-a]Quinoxalin-5(6H)-One A solution of 2 g. (0.01 mole) of 2,3,4,4a-tetrahydro-1H-pyrazino[1,2-a]quinoxalin-5(6H)-one and 3.2 g. (0.03 mole) of 4-vinylpyridine in 50 ml. of methanol containing 1.3 g. glacial acetic acid was heated under reflux for 24 hours. The reaction was allowed to cool, and the solvent was removed under reduced pressure (<5 mm.). The oily residue was taken up in water (25–30 ml.). Potassium carbonate was added until the solution was basic. The product was extracted into chloroform, and the chloroform solution was washed with saline, dried over magnesium sulfate, and filtered. The filtrate was treated with dry hydrogen chloride. The product hydrochloride was filtered off. Crude yield was 3.5 g. of material melting at 188°–92° C.

Recrystallization from methanol gave 2 g. (~50%) of the title compound as the dihydrochloride salt, m.p. 184°–186° C.

Analysis for: $C_{18}H_{22}N_4OCl_2.H_2O$. Calculated: C, 54.14; H, 6.06; N, 14.03; Cl, 17.76. Found: C, 54.51; H, 5.71; N, 13.97; Cl, 18.04.

EXAMPLE 2

2,3,4,4a-Tetrahydro-3-[2-(2-Pyridinyl)Ethyl]-1H-Pyrazino[1,2-a]Quinoxalin-5(6H)-One 2,3,4,4a-Tetrahydro-1H-pyrazino[1,2-a]quinoxalin-5(6H)-one (7 g.) and 2-vinylpyridine (12 g.) in 150 ml. of methanol containing 5 ml. glacial acetic acid were heated under reflux for 24 hours. After removing solvent under reduced pressure, the residue was slurried with water and the insoluble material filtered off and washed with water. After drying there was obtained 9.3 g. of the title compound. A portion recrystallized from ethanol gave a m.p. of 167°–69° C.

Analysis for: $C_{18}H_{20}N_4O$. Calculated: C, 70.10; H, 6.53; N, 18.17. Found: C, 69.77; H, 6.59; N, 17.86.

TLC showed 1 spot on a silica plate (1:2=MeOH:-Benzene). The hydrochloride was formed by treatment of an ethanolic solution of the base with dry hydrogen chloride till acidic. Precipitate was filtered off, washed with ethanol, ether, and dried. Recrystallized from ethanol and dried over $P_2O_5$. The m.p. of the dihydrochloride salt was 183°–185° C.

Analysis for: $C_{18}H_{20}N_4O.2HCl.\frac{1}{2}H_2O$. Calculated: C, 55.39; H, 5.94; N, 14.35; Cl, 18.17. Found: C, 55.55; H, 6.43; N, 14.43; Cl, 18.50.

EXAMPLE 3

8-Fluoro-2,3,4,4a-Tetrahydro-3-[2-(4-Pyridinyl)Ethyl]-1H-Pyrazino[1,2-a]Quinoxalin-5(6H)-One

Treating 2.3 g. of 8-fluoro-2,3,4,4a-tetrahydro-1H-pyrazino[1,2-a]quinoxaline-5(6H)-one with 9.0 g. of 4-vinylpyridine in the manner shown in Example 1, there was obtained 1.5 g. of the title compound as the dihydrochloride salt, m.p. 230°–233° C. (dec.).

Analysis for: $C_{18}H_{19}FN_4O.2HCl$. Calculated: C, 54.13; H, 5.30; N, 14.03; Cl, 17.76. Found: C, 53.47; H, 5.53; N, 13.74; Cl, 17.53.

EXAMPLE 4

8,9-Dichloro-2,3,4,4a-Tetrahydro-3-[2-(4-Pyridinyl)Ethyl]-1H-Pyrazino[1,2-a]Quinoxaline-5(6H)-One

Treatment of 8,9-dichloro-2,3,4,4a-tetrahydro-1H-pyrazino-[1,2-a]quinoxalin-5(6H)-one (3 g.) with 5.4 g. of 4-vinylpyridine in the manner described in Example 1 gave 2.2 g. of the title compound as the dihydrochloride salt, m.p. 266°–269° C. (dec.).

Analysis for: $C_{18}H_{18}N_4Cl_2O.2HCl.H_2O$. Calculated: C, 46.18; H, 4.73; N, 11.92; Cl, 30.29. Found: C, 46.50; H, 4.45; N, 12.01; Cl, 30.66.

EXAMPLE 5

2,3,4,4a-Tetrahydro-3-[2-(4-Pyridinyl)Ethyl]-8-Trifluoromethyl-1H-Pyrazino[1,2-a]Quinoxalin-5(6H)-One

A solution of 9.0 g. of 2,3,4,4a-tetrahydro-8-trifluoromethyl-1H-pyrazino[1,2-a]quinoxalin-5(6H)-one, 18 ml. of 4-vinylpyridine and 7 ml. of acetic acid was refluxed in 250 ml. of methanol overnight. The solvent was removed and the residue was precipitated with water. The precipitate was filtered and recrystallized from ethanol-water to yield 9.2 g. of the free base, m.p. 204°–206° C. 4 G. of this free base was dissolved in ethanol and treated with dry hydrogen chloride saturated ethanol. The product hydrogen chloride salt was filtered and recrystallized once from i-propanol and once from ethanol to yield 3.4 g. of the dihydrochloride salt of the title compound, m.p. 218°–221° C.

Analysis for: $C_{19}H_{19}F_3N_4O.2HCl.\frac{1}{2}H_2O$. Calculated: C, 49.79; H, 4.84; N, 12.22; Cl, 15.47. Found: C, 49.57; H, 4.95; N, 12.13; Cl, 15.49.

EXAMPLE 6

2,3,4,4a-Tetrahydro-3-[2-(2-Pyridinyl)Ethyl]-8-Trifluoromethyl-1H-Pyrazino[1,2-a]Quinoxalin-5(6H)-One

A solution of 8.5 g. (0.03 mole) of 2,3,4,4a-tetrahydro-8-trifluoromethyl-1H-pyrazino[1,2-a]quinoxalin-5(6H)-one and 17.5 g. (0.16 mole) of 2-vinylpyridine in 250 ml. of methanol containing 7 ml. acetic acid was heated under reflux for 20 hours. The reaction mixture was cooled, and the solvent was removed under reduced pressure. The residue was precipitated with 1 l. of water. The product was filtered and recrystallized from methanol-water to yield 10.1 g. of free base. 4.5 G. of this free base was dissolved in 150 ml. of absolute ethanol and treated with dry hydrogen chloride saturated ether solution. The product hydrochloride was filtered and recrystallized two times from methanol-ether to give 4 g. (71%) of the title compound as the dihydrochloride salt, m.p. 194°–196° C.

Analysis for: $C_{19}H_{19}F_3N_4O.2HCl.\frac{1}{2}H_2O$. Calculated: C, 50.01; H, 4.41; N, 12.28; Cl, 15.54. Found: C, 50.02; H, 4.58; N, 12.41; Cl, 15.60.

EXAMPLE 7

2,3,4,4a-Tetrahydro-3-[(4-Pyridinyl)Methyl]-1H-Pyrazino[1,2-a]Quinoxalin-5(6H)-One

A solution of 2,3,4,4a-tetrahydro-1H-pyrazino[1,2-a]quinoxalin-5(6H)-one 6.1 g. (0.03 mole) and 4.92 g. (0.03 mole) of 4-picolyl chloride hydrochloride, 10 g. of potassium carbonate, 0.5 ml. of tirethylamine in 200 ml. of acetone was refluxed for 40 hours with stirring. The reaction mixture was allowed to cool and the precipitate was filtered and washed with acetone. The acetone was removed under reduced pressure and the oily residue was dissolved in methylene chloride. This solution was washed with water, dried over magnesium sulfate, filtered and the solvent removed. The residue was dissolved in ethanol and treated with dry hydrogen chloride. The product hydrogen chloride was filtered and recrystallized from methanol to give 2 g. of the title compound as the dihydrochloride salt, m.p. 253°–255° C.

Analysis for: $C_{17}H_{18}N_4O.2HCl.\frac{1}{2}H_2O$. Calculated: C, 54.26; H, 5.62; N, 14.89; Cl, 18.84. Found: C, 54.50; H, 5.49; N, 14.95; Cl, 18.68.

EXAMPLE 8

2,3,4,4a-Tetrahydro-3-[3-(4-Pyridinyl)Propyl]-1H-Pyrazino[1,2-a]Quinoxalin-5-(6H)-One

A solution of 6.1 g. (0.03 mole) of 2,3,4,4a-tetrahydro-1H-pyrazino[1,2-a]quinoxalin-5(6H)-one, 6.3 g. (0.04 mole) of 3-(4-pyridyl)-1-chloropropane, 10 g. of potassium carbonate, 5 g. of potassium iodide and 0.5 ml. of triethylamine was stirred and refluxed in 200 ml. of acetone for 48 hours, then cooled and filtered. The solvent was removed, and the residue was dissolved in ethanol-ether and treated with dry hydrogen chloride saturated ether. The product hyrochloride was filtered and recrystallized two times from methanol. Dried at 100° C./0.1 mm. Yield: 6.2 g. (44%) as the dihydrochloride salt, m.p. 188°–190° C.

Analysis for: $C_{19}H_{22}N_4O.2HCl.1\frac{1}{2}H_2O$. Calculated: C, 54.04; H, 6.44; N, 13.26; Cl, 16.79. Found: C, 54.51; H, 6.49; N, 12.97; Cl, 16.76.

EXAMPLE 9

8-Fluoro-2,3,4,4a-Tetrahydro-3-[(4-Pyridinyl)Methyl]-1H-Pyrazino[1,2-a]Quinoxalin-5(6H)-One

A solution of 2 g. (0.008 mole) of 8-fluoro-2,3,4,4a-tetrahydro-1H-pyrazino[1,2-a]quinoxalin-5(6H)-one and 1.6 g. (0.01 mole) of 4-picolyl chloride, 3.5 g. of potassium carbonate and 0.5 ml. of triethylamine was stirred and refluxed in 100 ml. of acetone for 48 hours, cooled and filtered. The solvent was removed under reduced pressure. The residue was dissolved in ethanol and treated with dry hydrogen chloride saturated ether. The product hydrochloride was filtered and recrystallized from ethanol-water to yield 1.25 g. of the title compound as the dihydrochloride, m.p. 269°–272° C.

Analysis for: $C_{17}H_{17}FN_4O.2HCl$. Calculated: C, 52.99; H, 4.97; N, 14.54; Cl, 18.40. Found: C, 52.99; H, 4.65; N, 14.38; Cl, 18.42.

EXAMPLE 10

2,3,4,4a-Tetrahydro-3-[4-(4-Pyridinyl)Butyl]-1H-Pyrazino[1,2-a]Quinoxalin-5(6H)-One

A solution of 6.2 g. (0.03 mole) of 2,3,4,4a-tetrahydro-1H-pyrazino[1,2-a]quinoxalin-5(6H)-one, hydrochloride, 7 g. (0.04 mole) of 4-(4-pyridyl)-1-chlorobutane, 10 g. of potassium carbonate, 5 g. of potassium iodide and 0.5 ml. of triethylamine was stirred and refluxed in 200 ml. of acetone for 48 hours, cooled and filtered. The solvent was removed and the residue was dissolved in methylene chloride. This solution was washed with water and brine, dried over magnesium sulfate and filtered. The solvent was removed and the residue was chromatographed on 500 g. of Silicar, CC-7. Fractions eluted with 10% methanol in ethyl acetate afforded 3.2 g. of free base. 3 G. of the above free base was dissolved in ethanol and treated with dry hydrogen chloride saturated ether. The product hydrochloride was filtered and recrystallized from methanol to give 3.2 g. of the title compound as the dihydrochloride salt, m.p. 281°–283° C.

Analysis for: $C_{20}H_{24}N_4O.2HCl$. Calculated: C, 58.68; H, 6.40; N, 13.68; Cl, 17.32. Found: C, 58.52; H, 6.53; N, 13.74; Cl, 17.03.

EXAMPLE 11

8-Fluoro-2,3,4,4a-Tetrahydro-3-[4-(4-Pyridinyl)Butyl]-1H-Pyrazino[1,2-a]Quinoxalin-5(6H)-One A solution of 4.2 g. (0.02 mole) of 8-fluoro-2,3,4,4a-tetrahydro-1H-pyrazino[1,2-a]quinoxalin-5(6H)-one, 7 g. (0.04 mole) of 4-(4-pyridyl)-1-chlorobutane, 8 g. of potassium carbonate, 5 g. of potassium iodide, and 0.5 ml. of triethylamine was stirred and refluxed in 200 ml. of acetone for 72 hours, cooled and filtered. The solvent was removed and the residue was dissolved in methylene chloride. This solution was washed with water and brine, dried over magnesium sulfate and filtered. The solvent was removed and the residue was chromatographed on 500 g. of Silicar, CC-7. Fractions eluted with 10% methanol in ethyl acetate afforded the product as a free base. This free base was dissolved in ethanol and treated with dry hydrogen chloride saturated ether. The product hydrochloride was filtered and recrystallized from methanol to give 2.3 g. of the title compound as the dihydrochloride salt, m.p. 262°–264° C.

Analysis for: $C_{20}H_{23}FN_4O.2HCl$. Calculated: C, 56.20; H, 5.89; N, 13.11; Cl, 16.59. Found: C, 56.12; H, 6.12; N, 13.05; Cl, 16.20.

EXAMPLE 12

2,3,4,4a-Tetrahydro-6-Methyl-3-[(4-Pyridinyl)Methyl]-1H-Pyrazino[1,2-a]Quinoxalin-5(6H)-One A solution of 6 g. (0.03 mole) of 2,3,4,4a-tetrahydro-6-methyl-1H-pyrazino[1,2-a]quinoxalin-5(6H)-one, 5 g. (0.03 mole) of 4-picolyl chloride hydrochloride, 10 g. of potassium carbonate and 0.5 ml. of triethylamine was stirred and refluxed in 200 ml. of acetone overnight, cooled and filtered. The solvent was removed and the residue was dissolved in methylene chloride. This solution was washed with water and brine, dried over magnesium sulfate and filtered. The solvent was removed and the residue was chromatographed on 460 g. of Silicar, CC-7. Fractions eluted with 10% methanol in ethyl acetate afforded the product as a free base. This free base was dissolved in ethanol and treated with dry hydrogen chloride saturated ether. The product hydrochloride was filtered and recrystallized from methanol to yield 5.2 g. of the title compound as the dihydrochloride salt, m.p. 252°–254.5° C.

Analysis for: $C_{18}H_{20}N_4O.2NCl$. Calculated: C, 56.69; H, 5.81; N, 14.69; Cl, 18.58. Found: C, 56.53; H, 5.76; N, 14.65; Cl, 18.49.

EXAMPLE 13

2,3,4,4a-Tetrahydro-3-[5-(2-Pyridinyl)Pentyl]-1H-Pyrazino[1,2-a]Quinoxalin-5(6H)-One A solution of 6.2 g. (0.03 mole) of 2,3,4,4a-tetrahydro-1H-pyrazino[1,2-a]quinoxalin-5(6H)-one, hydrochloride, 7.5 g. (0.04 mole) of 5-(2-pyridyl)pentyl bromide hydrochloride, 15 g. potassium carbonate, 5 g. potassium iodide, and 0.5 ml. of triethylamine in acetone (200 ml.) is heated under reflux for 72 hours. The reaction is worked up in the usual manner, yielding the title compound as base. This is converted to dihydrochloride salt by treating an acetone solution of base with dry hydrogen chloride, m.p. 266°–69° C. (dec.).

Analysis for: $C_{21}H_{26}N_4O.2HCl$. Calculated: C, 59.56; H, 6.66; N, 13.23; Cl, 16.75. Found: C, 59.22; H, 6.72; N, 13.18; Cl, 16.70.

EXAMPLE 14

2,3,4,4a-Tetrahydro-3-[5-(4-Pyridinyl)Pentyl]-1H-Pyrazino[1,2-a]Quinoxalin-5(6H)-One To a solution of 6.2 g. (0.03 mole) of 2,3,4,4a-tetrahydro-1H-pyrazino[1,2-a]quinoxalin-5(6H)-one, hydrochloride in 200 ml. acetone is added 15 g. of powdered potassium carbonate, 0.5 ml. of triethylamine, 5 g. of potassium iodide, and 7 g. (0.038 mole) of 5-(4-pyridyl)pentyl bromide. The suspension is stirred and refluxed for 72 hours, cooled, and filtered. The filtrate is concentrated under reduced pressure and the residue is dissolved in methylene dichloride, washed with saline, and dried. The dried organic layer is concentrated and the residue purified by column chromatography using Silicar CC-7. This title compound is obtained as base and converted to hydrochloride salt.

EXAMPLE 15

2,3,4,4a-Tetrahydro-3-[2-(4-Piperidinyl)Ethyl]-1H-Pyrazino[1,2-a]Quinoxalin-5(6H)-One A solution of 2,3,4,4a-tetrahydro-3-[2-(4-pyridinyl)ethyl]-1H-pyrazino[1,2-a]quinoxalin-5(6H)-one in 120 ml. water and 60 ml. ethanol containing 13 ml. conc. hydrochloric acid was placed in a Parr hydrogenation apparatus, with 1.2 g. $PtO_2$, under 45 psi. of hydrogen and shaken till pressure drop ceased. After filtering off catalyst the solvents were removed under vacuum and the residue crystallized from hot ethanol. Product filtered off, washed (ethanol), and dried. Dissolved in hot methanol which was displaced by ethanol by boiling off lower boiling solvent. Yield: 4.0 g. of the title compound as the dihydrochloride salt, m.p. 238°–240° C.

Analysis for: $C_{18}H_{26}N_4O.2HCl.H_2O$. Calculated: C, 53.33; H, 7.45; N, 13.82; Cl, 17.49. Found: C, 53.06; H, 7.12; N, 13.77; Cl, 17.43.

EXAMPLE 16

2,3,4,4a-Tetrahydro-3-[2-(2-Piperidinyl)Ethyl]-1H-Pyrazino[1,2-a]Quinoxalin-5(6H)-One A solution of 2,3,4,4a-tetrahydro-3-[2-(2-pyridinyl)ethyl]-1H-pyrazino[1,2-a]quinoxalin-5(6H)-one in 120 ml. water and 60 ml. ethanol containing 14 ml. conc. hydrochloric acid, was shaken with 1.2 g. of $PtO_2$ under 45 psi. hydrogen pressure. Solution was filtered, concentrated under vacuum, and residue crystallized once from ethanol and then from methanol. After filtration and drying the dihydrochloride salt of the title compound had a m.p. of 268°–271° C. (dec.); yield: 3.5 g.

Analysis for: $C_{18}H_{26}N_4O.2HCl.\frac{1}{2}H_2O$. Calculated: C, 54.54; H, 7.37; N, 14.13; Cl, 17.89. Found: C, 54.34; H, 7.22; N, 14.24; Cl, 18.03.

EXAMPLE 17

8-Fluoro-2,3,4,4a-Tetrahydro-3-[2-(4-Piperidinyl)Ethyl]-1H-Pyrazino[1,2-a]Quinoxalin-5(6H)-One From 3 g. of 8-fluoro-2,3,4,4a-tetrahydro-3-[2-(4-pyridinyl)ethyl]-1H-pyrazino[1,2-a]quinoxalin-5(6H)-one treated in the same manner as Example 16, there was obtained 2.5 g. of product, the title compound as the dihydrochloride salt, m.p. 227°–230° C. (from ethanol).

Analysis for: $C_{18}H_{25}FN_4O.2HCl.H_2O$. Calculated: C, 49.88; H, 6.74; N, 12.93; Cl, 16.36. Found: C, 49.81; H, 6.48; N, 12.73; Cl, 6.10.

EXAMPLE 18

2,3,4,4a-Tetrahydro-3-[2-(4-[1-Diphenylmethyl]-Piperidinyl)-Ethyl]-1H-Pyrazino[1,2-a]Quinoxalin-5(6H)-One A suspension of 2,3,4,4a-tetrahydro-3-(2-[4-piperidinyl]-ethyl)-1H-pyrazino[1,2-a]quinoxalin-5(6H)-one 1.95 g. (0.005 mole), 2 g. potassium carbonate (powder), 5 drops triethylamine, and 1.5 g. diphenylmethyl bromide in 60 ml. dry acetone was heated under reflux for 4 days. Cooled, filtered, and the filtrate concentrated. The residue was then extracted with ether, and filtered. The ether layer was washed, dried and filtered. The ether filtrate was washed with saline and dried over sodium sulfate. After filtering the filtrate was treated with dry hydrogen chloride. A green precipitate formed and was filtered off, washed with ethanol, ether, and dried. Recrystallization from ethanol gave a green hydroscopic product. Recrystallization from 2-propanol gave 1.07 grams of product, m.p. 245°–7°. Recrystallization from methanol gave 0.5 g. of the title compound as the dihydrochloride salt; after drying at 60°/0.2 mm. for 18 hours, m.p. 282°–83° C. (dec.) was obtained.

Analysis for: $C_{31}H_{36}N_4O.2HCl.1\frac{1}{2}H_2O$. Calculated: C, 64.13; H, 7.12; N, 9.66; Cl, 12.21. Found: C, 63.68; H, 6.55; N, 9.61; Cl, 12.42.

EXAMPLE 19

2,3,4,4a-Tetrahydro-8-Trifluoromethyl-3-[2-(2-Piperidinyl)-Ethyl]-1H-Pyrazino[1,2-a]Quinoxalin-5(6H)-One A mixture of 5 g. (0.014 mole) of 2,3,4,4a-tetrahydro-3-[2-(2-pyridinyl)ethyl]-8-(trifluoromethyl)-1H-pyrazino[1,2-a]quinoxalin-5(6H)-one, 60 ml. of ethanol, 120 ml. of water, 12 ml. of concentrated hydrogen chloride and 1 g. of platinum oxide catalyst is hydrogenated in a Parr apparatus for 2 hours. The catalyst is filtered and the solvents removed. The residue was crystallized from ethanol and recrystallized from methanol to yield 4.5 g. of the title compound as the dihydrochloride salt, m.p. 283°–286° C. (dec.).

Analysis for: $C_{19}H_{25}F_3N_4O.2HCl$. Calculated: C, 50.11; H, 5.98; N, 12.30; Cl, 15.57. Found: C, 50.27; H, 6.02; N, 12.20; Cl, 15.49.

EXAMPLE 20

2,3,4,4a-Tetrahydro-3-[2-(4-Piperidinyl)Ethyl]-8-(Trifluoromethyl)-1H-Pyrazino[1,2-a]Quinoxalin-5(6H)-One A mixture of 5 g. (0.014 mole) of 2,3,4,4a-tetrahydro-3-[2-(4-pyridinyl)ethyl]-8-trifluoromethyl-1H-pyrazino[1,2-a]quinoxalin-5(6H)-one, 60 ml. of ethanol, 120 ml. of water, 12 ml. of concentrated hydrochloric acid and 1 g. of platinum oxide catalyst was hydrogenated in a Parr apparatus for 2 hours. The catalyst was filtered and the solvents removed. The residue was crystallized two times from methanol to yield 42 g. of the title compound as the dihydrochloride salt, m.p. 279°–282° C.

Analysis for: $C_{19}H_{25}F_3N_4O.2HCl.CH_3OH$. Calculated: C, 49.30; H, 6.41; N, 11.48; Cl, 14.54. Found: C, 49.77; H, 6.50; N, 11.65; Cl, 14.64.

What is claimed is:

1. A compound of the formula:

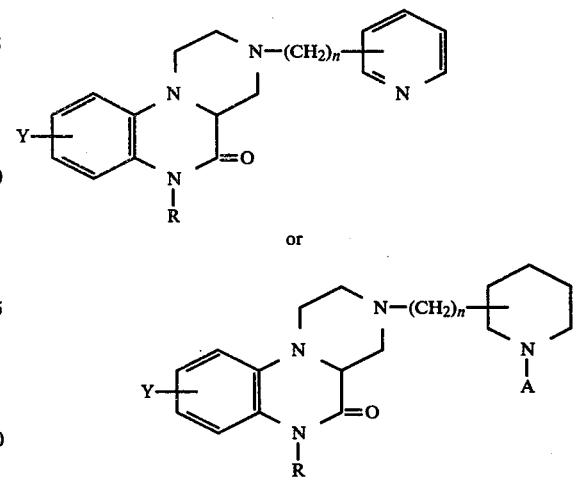

wherein
n is an integer from 1 to 8;
R is hydrogen or lower alkyl;
Y is hydrogen, lower alkyl, lower alkoxy, chlorine, fluorine, or trifluoromethyl, in the 7, 8, or 9 position;
A is hydrogen, lower alkyl, phen(lower)alkyl, or diphenyl(lower)alkyl; and
the pyridinyl or piperidinyl moiety is joined to the alkylene bridging group at the 2 or 4 position; or
a non-toxic acid addition salt thereof.

2. A pyridinylalkyl compound as defined in claim 1 in which n is 1 to 5.

3. A compound as defined in claim 2 in which Y is hydrogen, fluorine or trifluoromethyl.

4. A compound as defined in claim 2 in which Y is in the 8 position.

5. A compound as defined in claim 2 in which R is hydrogen.

6. A compound as defined in claim 3 in which R is methyl.

7. A compound as defined in claim 2 which is 2,3,4,4a-tetrahydro-3-[2-(4-pyridinyl)ethyl]-1H-pyrazino[1,2-a]quinoxalin-5(6H)-one or a non-toxic acid addition salt thereof.

8. A compound as defined in claim 2 which is 2,3,4,4a-tetrahydro-3-[2-(2-pyridinyl)ethyl]-1H-pyrazino[1,2-a]quinoxalin-5(6H)-one or a non-toxic acid addition salt thereof.

9. A compound as defined in claim 2 which is 8fluoro-2,3,4,4a-tetrahydro-3-[2-(4-pyridinyl)ethyl]-1H-pyrazino[1,2-a]-quinoxalin-5(6H)-one or a non-toxic acid addition salt thereof.

10. A compound as defined in claim 2 which is 8,9-dichloro-2,3,4,4a-tetrahydro-3-[2-(4-pyridinyl)ethyl]-1H-pyrazino-[1,2-a]quinoxalin-5(6H)-one or a non-toxic acid addition salt thereof.

11. A compound as defined in claim 2 which is 2,3,4,4a-tetrahydro-3-[2-(4-pyridinyl)ethyl]-8-trifluoromethyl-1H-pyrazino[1,2-a]quinoxalin-5(6H)-one or a non-toxic acid addition salt thereof.

12. A compound as defined in claim 2 which is 2,3,4,4a-tetrahydro-8-trifluoromethyl-3-[2-(2-pyridinyl)ethyl]-1H-pyrazino-[1,2-a]quinoxalin-5(6H)-one or a non-toxic acid addition salt thereof.

13. A compound as defined in claim 2 which is 2,3,4,4a-tetrahydro-3-[(4-pyridinyl)methyl]-1H-pyrazino[1,2-a]quinoxalin-5(6H)-one or a non-toxic acid addition salt thereof.

14. A compound as defined in claim 2 which is 2,3,4,4a-tetrahydro-3-[3-(4-pyridinyl)propyl]-1H-pyrazino[1,2-a]quinoxalin-5(6H)-one or a non-toxic acid addition salt thereof.

15. A compound as defined in claim 2 which is 8-fluoro-2,3,4,4a-tetrahydro-3-[(4-pyridinyl)methyl]-1H-pyrazino[1,2-a]-quinoxalin-5(6H)-one or a non-toxic acid addition salt thereof.

16. A compound as defined in claim 2 which is 2,3,4,4a-tetrahydro-3-[4-(4-pyridinyl)butyl]-1H-pyrazino[1,2-a]quinoxalin-5(6H)-one or a non-toxic acid addition salt thereof.

17. A compound as defined in claim 2 which is 8-fluoro-2,3,4,4a-tetrahydro-3-[4-(4-pyridinyl)butyl]-1H-pyrazino[1,2-a]-quinoxalin-5(6H)-one or a non-toxic acid addition salt thereof.

18. A compound as defined in claim 2 which is 2,3,4,4a-tetrahydro-6-methyl-3-[(4-pyridinyl)methyl]-1H-pyrazino[1,2-a]quinoxalin-5(6H)-one or a non-toxic acid addition salt thereof.

19. A compound as defined in claim 2 which is 2,3,4,4a-tetrahydro-3-[5-(2-pyridinyl)pentyl]-1H-pyrazino[1,2-a]quinoxalin-5(6H)-one or a non-toxic acid addition salt thereof.

20. A compound as defined in claim 2 which is 2,3,4,4a-tetrahydro-3-[5-(4-pyridinyl)pentyl]-1H-pyrazino[1,2-a]quinoxalin-5(6H)-one or a non-toxic acid addition salt thereof.

21. A piperidinylalkyl compound as defined in claim 1 in which n is 1 to 5.

22. A compound as defined in claim 21 in which Y is hydrogen, fluorine or trifluoromethyl.

23. A compound as defined in claim 21 in which Y is in the 8 position.

24. A compound as defined in claim 22 in which R is hydrogen.

25. A compound as defined in claim 21 in which A is hydrogen or diphenylmethyl.

26. A compound as defined in claim 21 in which R is methyl.

27. A compound as defined in claim 21 in which n is 2.

28. A compound as defined in claim 21 which is 2,3,4,4a-tetrahydro-3-[2-(4-piperidinyl)ethyl]-1H-pyrazino[1,2-a]quinoxalin-5(6H)-one or a non-toxic acid addition salt thereof.

29. A compound as defined in claim 21 which is 2,3,4,4a-tetrahydro-3-[2-(2-piperidinyl)ethyl]-1H-pyrazino[1,2-a]quinoxalin-5(6H)-one or a non-toxic acid addition salt thereof.

30. A compound as defined in claim 21 which is 8-fluoro-2,3,4,4a-tetrahydro-3-[2-(4-piperidinyl)ethyl]-1H-pyrazino[1,2-a]-quinoxalin-5(6H)-one or a non-toxic acid addition salt thereof.

31. A compound as defined in claim 21 which is 2,3,4,4a-tetrahydro-3-[2-(4-[1-diphenylmethyl]-piperidinyl)ethyl]-1H-pyrazino[1,2-a]quinoxalin-5(6H)-one.

32. A compound as defined in claim 21 which is 2,3,4,4a-tetrahydro-8-trifluoromethyl-3-[2-(2-piperidinyl)ethyl]-1H-pyrazino-[1,2-a]quinoxalin-5(6H)-one or a non-toxic acid addition salt thereof.

33. A compound as defined in claim 21 which is 2,3,4,4a-tetrahydro-3-[2-(4-piperidinyl)ethyl]-8-trifluoromethyl-1H-pyrazino[1,2-a]quinoxalin-5(6H)-one or a non-toxic acid addition salt thereof.

34. A method for relieving hypertension in warm-blooded animals which comprises administering to an animal in need thereof an anti-hypertensive effective amount of a compound of the formula:

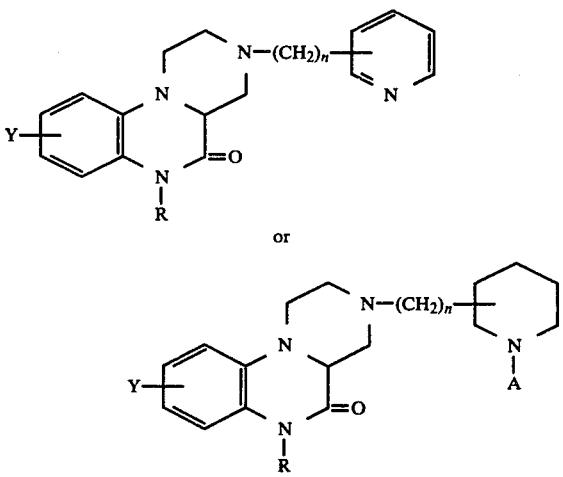

wherein
n is an integer from 1 to 8;
R is hydrogen or lower alkyl;
Y is hydrogen, lower alkyl, lower alkoxy, chlorine, fluorine, or trifluoromethyl in the 7, 8, or 9 position;
A is hydrogen, lower alkyl, phen(lower)alkyl, or diphenyl-(lower)alkyl; and
the pyridinyl or piperidinyl moiety is joined to the alkylene bridging group at the 2 or 4 position; or
a non-toxic acid addition salt thereof.

35. A method as defined in claim 34 in which the compound is a pyridinylalkyl compound thereof wherein n is 1 to 5.

36. A method as defined in claim 35 wherein Y is hydrogen, fluorine, or trifluoromethyl.

37. A method as defined in claim 35 wherein Y is in the 8 position.

38. A method as defined in claim 35 wherein R is hydrogen.

39. A method as defined in claim 36 wherein R is methyl.

40. A method as defined in claim 35 wherein the compound is 2,3,4,4a-tetrahydro-3-[2-(2-pyridinyl)ethyl]-1H-pyrazino-[1,2-a]quinoxalin-5(6H)-one or a non-toxic acid addition salt thereof.

41. A method as defined in claim 35 wherein the compound is 8-fluoro-2,3,4,4a-tetrahydro-3-[2-(4-pyridinyl)ethyl]-1H-pyrazino[1,2-a]-quinoxalin-5(6H)-one or a non-toxic acid addition salt thereof.

42. A method as defined in claim 35 wherein the compound is 2,3,4,4a-tetrahydro-8-trifluoromethyl-3-[2-(2-pyridinyl)-ethyl]-1H-pyrazino-[1,2-a]quinoxalin-5(6H)-one or a non-toxic acid addition salt thereof.

43. A method as defined in claim 35 wherein the compound is 2,3,4,4a-tetrahydro-3-[(4-pyridinyl)methyl]-1H-pyrazino[1,2-a]quinoxalin-5(6H)-one or a non-toxic acid addition salt thereof.

44. A method as defined in claim 35 wherein a compound is 2,3,4,4a-tetrahydro-3-[3-(4-pyridinyl)propyl]-1H-pyrazino-[1,2-a]quinoxalin-5(6H)-one or a non-toxic acid addition salt thereof.

45. A method as defined in claim 35 wherein the compound is 8-fluoro-2,3,4,4a-tetrahydro-3-[(4-pyridinyl)methyl]-1H-pyrazino[1,2-a]-quinoxalin-5(6H)-one or a non-toxic acid addition salt thereof.

46. A method as defined in claim 35 wherein the compound is 2,3,4,4a-tetrahydro-3-[4-(4-pyridinyl)butyl]-1H-pyrazino-[1,2-a]quinoxalin-5(6H)-one or a non-toxic acid addition salt thereof.

47. A method as defined in claim 35 wherein the compound is 8-fluoro-2,3,4,4a-tetrahydro-3-[4-(4-pyridinyl)butyl]-1H-pyrazino[1,2-a]quinoxalin-5(6H)-one or a non-toxic acid addition salt thereof.

48. A method as defined in claim 35 wherein the compound is 2,3,4,4a-tetrahydro-6-methyl-3-[(4-pyridinyl)methyl]-1H-pyrazino[1,2-a]quinoxalin-5(6H)-one or a non-toxic acid addition salt thereof.

49. A method as defined in claim 35 wherein the compound is 2,3,4,4a-tetrahydro-3-[5-(2-pyridinyl)pentyl]-1H-pyrazino-[1,2-a]quinoxalin-5(6H)-one or a non-toxic acid addition salt thereof.

50. A method as defined in claim 35 wherein the compound is 2,3,4,4a-tetrahydro-3-[5-(4-pyridinyl)-pentyl]-1H-pyrazino[1,2-a]quinoxalin-5(6H)-one or a non-toxic acid addition salt thereof.

51. A method as defined in claim 34 in which the compound is a piperidinylalkyl compound thereof wherein n is 1 to 4.

52. A method as defined in claim 51 wherein the compound is 2,3,4,4a-tetrahydro-3-[2-(4-piperidinyl)ethyl]-1H-pyrazino[1,2-a]quinoxalin-5(6H)-one or a non-toxic acid addition salt thereof.

53. A method as defined in claim 51 wherein the compound is 3-[2-[1-(diphenylmethyl)-4-piperidinyl]ethyl]-1H-pyrazino[1,2-a]quinoxalin-5(6H)-one or a non-toxic acid addition salt thereof.

54. A method as defined in claim 51 wherein the compound is 2,3,4,4a-tetrahydro-8-trifluoromethyl-3-[2-(2-piperidinyl)-ethyl]-1H-pyrazino[1,2-a]quinoxalin-5(6H)-one or a non-toxic acid addition salt thereof.

* * * * *